United States Patent
Hecker et al.

(10) Patent No.: US 9,492,305 B2
(45) Date of Patent: Nov. 15, 2016

(54) ORTHOPEDIC WALKING BOOT WITH HEEL CUSHION

(71) Applicant: OVATION MEDICAL, Agoura Hills, CA (US)

(72) Inventors: Steven L. Hecker, Los Angeles, CA (US); Tracy E. Grim, Thousand Oaks, CA (US); Kenji Watabe, Ventura, CA (US); Ryan C. Cohn, Torrance, CA (US); Tim Crowley, Ventura, CA (US); Veneza Yuzon, Calabasas, CA (US)

(73) Assignee: Ortho Systems, Agoura Hills, CA (US)

(*) Notice: Subject to any disclaimer, the term of this patent is extended or adjusted under 35 U.S.C. 154(b) by 300 days.

(21) Appl. No.: 14/214,238

(22) Filed: Mar. 14, 2014

(65) Prior Publication Data
US 2014/0310993 A1 Oct. 23, 2014

Related U.S. Application Data

(60) Provisional application No. 61/801,961, filed on Mar. 15, 2013, provisional application No. 61/916,080, filed on Dec. 13, 2013.

(51) Int. Cl.
*A43B 23/28* (2006.01)
*A61F 5/01* (2006.01)
*A61F 5/058* (2006.01)

(52) U.S. Cl.
CPC .............. *A61F 5/0195* (2013.01); *A43B 23/28* (2013.01); *A61F 5/0585* (2013.01)

(58) Field of Classification Search
CPC ....................... A61F 5/01; A61F 5/0111; A61F 5/0127; A61F 5/0195; A43B 3/18; A43B 23/28; A43B 23/30
USPC .................................. 36/110, 69, 58.5, 58.6
See application file for complete search history.

(56) References Cited

U.S. PATENT DOCUMENTS

| 143,537 | A | | 10/1873 | Silberschmidt | |
|---|---|---|---|---|---|
| 395,271 | A | * | 12/1888 | Fry | A43B 3/16 36/58.6 |
| 447,564 | A | * | 3/1891 | Egley | A43B 23/28 36/58.5 |
| 699,800 | A | * | 5/1902 | King | A43B 3/16 36/58.6 |

(Continued)

FOREIGN PATENT DOCUMENTS

| CN | 201085714 Y | 7/2008 |
|---|---|---|
| CN | 201523712 U | 7/2010 |

(Continued)

OTHER PUBLICATIONS

PCT Publication No. WO/87/03471, dated Jun. 18, 1987, regarding PCT Application No. PCT/US86/02670.

(Continued)

*Primary Examiner* — Marie Bays
(74) *Attorney, Agent, or Firm* — Arent Fox LLP

(57) ABSTRACT

An orthopedic walking boot, comprising a base to support a user's foot, the base having a section configured to support the user's posterior portion of the heel; a support assembly extending from the base to support the user's lower leg; and a heel cushion arranged with said section of the base to engage the user's posterior portion of the heel, the heel portion having a free edge configured to flex.

18 Claims, 10 Drawing Sheets

(56) References Cited

U.S. PATENT DOCUMENTS

| | | | |
|---|---|---|---|
| 1,023,877 | A * | 4/1912 | Rogers .................. A43B 23/28 36/58.5 |
| 1,472,415 | A | 10/1923 | Haggerty |
| 1,524,805 | A * | 2/1925 | Anderson ............... A43B 3/18 36/58.6 |
| 2,643,468 | A | 6/1953 | Gottschalk |
| 2,959,169 | A | 11/1960 | Bless |
| 3,006,084 | A * | 10/1961 | Le Compte .............. A43B 3/02 36/3 A |
| 3,464,126 | A | 9/1969 | Sarkissian |
| 3,504,668 | A | 4/1970 | Boudon |
| 3,661,151 | A | 5/1972 | Schoenbrun et al. |
| 3,665,619 | A | 5/1972 | Gray |
| 3,792,537 | A | 2/1974 | Plank et al. |
| 3,805,773 | A | 4/1974 | Sichau |
| 3,814,088 | A | 6/1974 | Raymond |
| 3,905,135 | A * | 9/1975 | Debusk ................. A61F 13/043 36/110 |
| 3,955,565 | A | 5/1976 | Johnson |
| 3,976,059 | A | 8/1976 | Lonardo |
| 4,005,704 | A | 2/1977 | Stöhr et al. |
| 4,053,995 | A | 10/1977 | Shein |
| 4,057,056 | A | 11/1977 | Payton |
| 4,094,312 | A | 6/1978 | Whyte |
| 4,100,686 | A | 7/1978 | Sgarlato et al. |
| 4,100,918 | A | 7/1978 | Glancy |
| 4,184,273 | A | 1/1980 | Boyer et al. |
| 4,188,735 | A | 2/1980 | Hahn |
| 4,215,491 | A | 8/1980 | Giannetti |
| 4,217,706 | A | 8/1980 | Vartanian |
| 4,265,033 | A | 5/1981 | Pois |
| 4,268,931 | A | 5/1981 | Salomon |
| 4,393,866 | A | 7/1983 | Finnieston |
| 4,446,856 | A | 5/1984 | Jordan |
| 4,454,871 | A | 6/1984 | Mann et al. |
| 4,494,536 | A | 1/1985 | Latenser |
| 4,497,070 | A | 2/1985 | Cho |
| 4,503,628 | A * | 3/1985 | Mancinelli ............. A43B 23/28 36/58.6 |
| 4,505,269 | A | 3/1985 | Davies et al. |
| 4,510,927 | A | 4/1985 | Peters |
| 4,550,721 | A | 11/1985 | Michel |
| 4,556,054 | A | 12/1985 | Paulseth |
| 4,559,934 | A | 12/1985 | Philipp |
| 4,567,678 | A | 2/1986 | Morgan et al. |
| 4,572,169 | A | 2/1986 | Mauldin et al. |
| 4,587,962 | A | 5/1986 | Greene et al. |
| 4,590,932 | A | 5/1986 | Wilkerson |
| 4,622,764 | A * | 11/1986 | Boulier ................. A43B 23/17 36/68 |
| 4,624,247 | A | 11/1986 | Ford |
| 4,628,945 | A | 12/1986 | Johnson, Jr. |
| 4,665,904 | A | 5/1987 | Lerman |
| 4,771,768 | A | 9/1988 | Crispin |
| 4,805,601 | A | 2/1989 | Eischen, Sr. |
| 4,825,856 | A | 5/1989 | Nelson |
| 4,844,094 | A | 7/1989 | Grim |
| 4,862,900 | A | 9/1989 | Hefele |
| 4,872,273 | A | 10/1989 | Smeed |
| 4,879,822 | A | 11/1989 | Hayes |
| 4,919,118 | A | 4/1990 | Morris |
| 4,941,271 | A | 7/1990 | Lakic |
| 4,947,838 | A | 8/1990 | Giannetti |
| 4,964,402 | A | 10/1990 | Grim et al. |
| 4,974,583 | A | 12/1990 | Freitas |
| 4,982,733 | A | 1/1991 | Broadhurst et al. |
| 4,999,932 | A | 3/1991 | Grim |
| 5,020,523 | A | 6/1991 | Bodine |
| 5,078,128 | A | 1/1992 | Grim et al. |
| 5,086,761 | A | 2/1992 | Ingram |
| 5,088,478 | A | 2/1992 | Grim |
| 5,088,479 | A | 2/1992 | Detoro |
| 5,088,481 | A | 2/1992 | Darby |
| 5,092,321 | A | 3/1992 | Spademan |
| 5,125,400 | A | 6/1992 | Johnson, Jr. |
| 5,154,695 | A | 10/1992 | Farris et al. |
| 5,176,623 | A | 1/1993 | Stetman et al. |
| 5,197,942 | A | 3/1993 | Brady |
| 5,213,564 | A | 5/1993 | Johnson, Jr. et al. |
| 5,219,324 | A | 6/1993 | Hall |
| 5,226,245 | A | 7/1993 | Lamont |
| 5,226,875 | A | 7/1993 | Johnson |
| 5,233,767 | A | 8/1993 | Kramer |
| 5,242,379 | A | 9/1993 | Harris et al. |
| 5,277,695 | A | 1/1994 | Johnson, Jr. et al. |
| RE34,661 | E | 7/1994 | Grim |
| 5,329,705 | A | 7/1994 | Grim et al. |
| 5,330,419 | A | 7/1994 | Toronto |
| 5,334,135 | A | 8/1994 | Grim et al. |
| 5,352,189 | A | 10/1994 | Schumann et al. |
| 5,353,525 | A | 10/1994 | Grim |
| 5,367,789 | A | 11/1994 | Lamont |
| 5,368,551 | A | 11/1994 | Zuckerman |
| 5,370,133 | A | 12/1994 | Darby et al. |
| 5,370,604 | A | 12/1994 | Bernardoni |
| 5,378,223 | A | 1/1995 | Grim et al. |
| 5,383,290 | A | 1/1995 | Grim |
| 5,384,970 | A | 1/1995 | Melton |
| 5,392,534 | A | 2/1995 | Grim |
| 5,399,152 | A | 3/1995 | Habermeyer et al. |
| 5,399,155 | A | 3/1995 | Strassburg et al. |
| 5,407,421 | A | 4/1995 | Goldsmith |
| 5,425,701 | A | 6/1995 | Oster et al. |
| 5,426,872 | A | 6/1995 | Hayes |
| 5,429,588 | A | 7/1995 | Young et al. |
| 5,441,015 | A | 8/1995 | Farley |
| 5,445,602 | A | 8/1995 | Grim et al. |
| 5,460,599 | A | 10/1995 | Davis et al. |
| 5,464,385 | A | 11/1995 | Grim |
| 5,483,757 | A | 1/1996 | Frykberg |
| 5,496,263 | A | 3/1996 | Fuller, II et al. |
| 5,503,622 | A | 4/1996 | Wehr |
| 5,507,720 | A | 4/1996 | Lampropoulos |
| 5,526,586 | A | 6/1996 | Foscaro |
| 5,527,269 | A | 6/1996 | Reithofer |
| 5,551,950 | A | 9/1996 | Oppen |
| 5,554,104 | A | 9/1996 | Grim |
| 5,571,077 | A | 11/1996 | Klearman et al. |
| 5,577,998 | A | 11/1996 | Johnson, Jr. et al. |
| 5,582,579 | A | 12/1996 | Chism et al. |
| 5,609,570 | A | 3/1997 | Lamont |
| 5,617,650 | A | 4/1997 | Grim |
| 5,620,411 | A | 4/1997 | Schumann et al. |
| 5,632,723 | A | 5/1997 | Grim |
| 5,641,322 | A | 6/1997 | Silver et al. |
| 5,675,839 | A | 10/1997 | Gordon et al. |
| 5,761,834 | A | 6/1998 | Grim et al. |
| 5,762,622 | A | 6/1998 | Lamont |
| 5,772,619 | A | 6/1998 | Corbett |
| 5,776,090 | A | 7/1998 | Bergmann et al. |
| 5,799,659 | A | 9/1998 | Stano |
| 5,813,143 | A * | 9/1998 | Bell ...................... A43C 15/06 36/59 R |
| 5,823,981 | A | 10/1998 | Grim et al. |
| 5,827,210 | A | 10/1998 | Antar et al. |
| 5,827,211 | A | 10/1998 | Sellinger |
| 5,833,639 | A | 11/1998 | Nune et al. |
| 5,836,902 | A | 11/1998 | Gray |
| 5,853,381 | A | 12/1998 | Stevenson et al. |
| 5,857,987 | A | 1/1999 | Habermeyer |
| 5,865,166 | A | 2/1999 | Fitzpatrick et al. |
| 5,868,690 | A | 2/1999 | Eischen, Sr. |
| 5,887,591 | A | 3/1999 | Powell et al. |
| 5,891,073 | A | 4/1999 | Deirmendjian et al. |
| 5,897,515 | A | 4/1999 | Willner et al. |
| 5,897,520 | A | 4/1999 | Gerig |
| 5,902,259 | A | 5/1999 | Wilkerson |
| 5,913,841 | A | 6/1999 | Lamont |
| 5,925,010 | A | 7/1999 | Caprio, Jr. |
| 5,951,504 | A | 9/1999 | Iglesias et al. |
| 5,954,075 | A | 9/1999 | Gilmour |
| 5,961,477 | A | 10/1999 | Turtzo |
| 5,980,475 | A | 11/1999 | Gibbons |

(56) References Cited

U.S. PATENT DOCUMENTS

| | | | |
|---|---|---|---|
| 5,993,404 A | 11/1999 | Mc Niel | |
| 6,019,741 A | 2/2000 | Prieskorn | |
| 6,021,780 A | 2/2000 | Darby | |
| 6,024,712 A | 2/2000 | Iglesia et al. | |
| 6,027,468 A | 2/2000 | Pick | |
| 6,044,578 A | 4/2000 | Kelz | |
| 6,056,712 A | 5/2000 | Grim | |
| 6,126,625 A | 10/2000 | Lundberg | |
| 6,154,983 A | 12/2000 | Austin | |
| 6,155,998 A | 12/2000 | Gilmour | |
| 6,189,172 B1 | 2/2001 | Baek | |
| 6,228,044 B1 | 5/2001 | Jensen et al. | |
| 6,247,250 B1 | 6/2001 | Hauser | |
| 6,267,742 B1 | 7/2001 | Krivosha et al. | |
| 6,277,087 B1 | 8/2001 | Hess et al. | |
| 6,282,816 B1 | 9/2001 | Rosendahl | |
| 6,282,818 B1 | 9/2001 | Lu | |
| 6,334,854 B1 | 1/2002 | Davis | |
| 6,350,246 B1 | 2/2002 | DeToro | |
| 6,361,514 B1 | 3/2002 | Brown et al. | |
| 6,361,515 B1 | 3/2002 | Gilmour | |
| 6,374,516 B1 | 4/2002 | Bonaventure et al. | |
| 6,406,450 B1 | 6/2002 | Kowalczyk et al. | |
| 6,409,695 B1 | 6/2002 | Connelly | |
| 6,432,073 B2 | 8/2002 | Prior et al. | |
| 6,491,654 B2 | 12/2002 | Lamont | |
| D473,654 S | 4/2003 | Iglesias et al. | |
| 6,558,339 B1 | 5/2003 | Graham | |
| 6,572,571 B2 | 6/2003 | Lowe | |
| 6,648,843 B1 | 11/2003 | Marciano et al. | |
| 6,656,145 B1 | 12/2003 | Morton | |
| 6,682,497 B2 | 1/2004 | Jensen et al. | |
| 6,699,209 B2 | 3/2004 | Turtzo | |
| 6,722,060 B2 | 4/2004 | Okajima | |
| 6,755,798 B2 | 6/2004 | McCarthy et al. | |
| 6,796,058 B2 | 9/2004 | Potchatko | |
| D500,855 S | 1/2005 | Pick et al. | |
| 6,866,043 B1 | 3/2005 | Davis | |
| 6,923,780 B2 | 8/2005 | Price et al. | |
| 6,945,946 B2 | 9/2005 | Rooney | |
| 6,945,947 B2 | 9/2005 | Ingimundarson et al. | |
| 6,955,654 B2 | 10/2005 | Gilmour | |
| 6,976,972 B2 | 12/2005 | Bradshaw | |
| 6,979,287 B2 | 12/2005 | Elbaz et al. | |
| 6,991,613 B2 | 1/2006 | Sensabaugh | |
| 7,018,351 B1 | 3/2006 | Iglesias et al. | |
| 7,018,352 B2 | 3/2006 | Pressman et al. | |
| D519,211 S | 4/2006 | Doty et al. | |
| 7,077,818 B2 | 7/2006 | Ingimundarson et al. | |
| 7,163,518 B1 | 1/2007 | Roche et al. | |
| 7,163,519 B2 | 1/2007 | Price et al. | |
| 7,182,743 B2 | 2/2007 | Slautterback et al. | |
| 7,188,438 B1 * | 3/2007 | Bowen | A43B 3/18 36/138 |
| D541,085 S | 4/2007 | Marsilio | |
| 7,288,076 B2 | 10/2007 | Grim et al. | |
| 7,294,114 B1 | 11/2007 | Clement et al. | |
| 7,303,538 B2 | 12/2007 | Grim et al. | |
| 7,311,686 B1 | 12/2007 | Iglesias et al. | |
| 7,354,411 B2 | 4/2008 | Perry et al. | |
| 7,384,584 B2 | 6/2008 | Jerome et al. | |
| 7,475,501 B1 | 1/2009 | DeToro et al. | |
| 7,563,238 B1 | 7/2009 | Breashears | |
| 7,569,022 B2 | 8/2009 | Morinaka | |
| 7,585,285 B2 | 9/2009 | Pone et al. | |
| 7,597,674 B2 | 10/2009 | Hu et al. | |
| 7,666,157 B2 | 2/2010 | Win | |
| D616,556 S | 5/2010 | Hu | |
| 7,727,173 B2 | 6/2010 | Rooney | |
| 7,727,174 B2 | 6/2010 | Chang et al. | |
| 7,743,532 B2 | 6/2010 | Bledsoe et al. | |
| D619,726 S | 7/2010 | Win | |
| 7,758,529 B2 | 7/2010 | Jensen et al. | |
| 7,867,182 B2 | 1/2011 | Iglesias et al. | |
| D634,438 S | 3/2011 | Hu | |
| 7,896,826 B2 | 3/2011 | Hu et al. | |
| 7,918,813 B2 | 4/2011 | Drake et al. | |
| D640,792 S | 6/2011 | Anderson et al. | |
| D641,084 S | 7/2011 | Anderson et al. | |
| D642,695 S | 8/2011 | Anderson et al. | |
| 8,002,724 B2 | 8/2011 | Hu et al. | |
| D645,153 S | 9/2011 | Anderson et al. | |
| 8,012,112 B2 | 9/2011 | Barberio | |
| D662,598 S | 6/2012 | Anderson et al. | |
| 8,215,030 B2 * | 7/2012 | Bowen | A43B 3/166 36/138 |
| 8,226,585 B2 | 7/2012 | Pick et al. | |
| 8,251,932 B2 | 8/2012 | Fout | |
| 8,251,936 B2 * | 8/2012 | Fout | A61F 5/0111 36/25 R |
| 8,932,245 B2 * | 1/2015 | Chen | A61F 5/0195 602/13 |
| 2002/0062579 A1 | 5/2002 | Caeran | |
| 2002/0128574 A1 | 9/2002 | Darby | |
| 2003/0136026 A1 * | 7/2003 | Crary | B29D 35/124 36/58.5 |
| 2003/0196352 A1 | 10/2003 | Bledsoe et al. | |
| 2004/0015112 A1 | 1/2004 | Salutterback et al. | |
| 2004/0030275 A1 | 2/2004 | Morinaka | |
| 2005/0172517 A1 | 8/2005 | Bledsoe et al. | |
| 2005/0228332 A1 | 10/2005 | Bushby | |
| 2005/0240133 A1 | 10/2005 | Rooney | |
| 2005/0274046 A1 | 12/2005 | Schwartz | |
| 2006/0032093 A1 | 2/2006 | Vannini | |
| 2006/0048344 A1 | 3/2006 | Cavanagh et al. | |
| 2006/0084899 A1 | 4/2006 | Verkade et al. | |
| 2006/0189907 A1 | 8/2006 | Pick et al. | |
| 2006/0217649 A1 | 9/2006 | Rabe | |
| 2007/0010770 A1 | 1/2007 | Gildersleeve | |
| 2007/0191749 A1 | 8/2007 | Barberio | |
| 2007/0260164 A1 | 11/2007 | Chiodo et al. | |
| 2007/0276307 A1 | 11/2007 | Erenstone | |
| 2008/0004558 A1 | 1/2008 | Outred et al. | |
| 2008/0098626 A1 | 5/2008 | Wright | |
| 2008/0154166 A1 | 6/2008 | Beckwith et al. | |
| 2008/0294082 A1 | 11/2008 | Chang et al. | |
| 2008/0294083 A1 | 11/2008 | Chang et al. | |
| 2008/0302371 A1 | 12/2008 | Cohen et al. | |
| 2008/0319362 A1 | 12/2008 | Joseph | |
| 2009/0043234 A1 | 2/2009 | Bledsoe et al. | |
| 2009/0076425 A1 | 3/2009 | Schwartz | |
| 2009/0192427 A1 | 7/2009 | Brown et al. | |
| 2009/0192428 A1 | 7/2009 | DeBoer et al. | |
| 2009/0227927 A1 | 9/2009 | Frazer | |
| 2009/0227928 A1 | 9/2009 | Drake et al. | |
| 2009/0264803 A1 | 10/2009 | Darby, II et al. | |
| 2009/0299246 A1 | 12/2009 | Pone et al. | |
| 2009/0306565 A1 | 12/2009 | Chan | |
| 2010/0069807 A1 | 3/2010 | Cox | |
| 2010/0100018 A1 | 4/2010 | Fout | |
| 2010/0204631 A1 | 8/2010 | Rooney | |
| 2010/0234782 A1 | 9/2010 | Hu et al. | |
| 2010/0324461 A1 | 12/2010 | Darby | |
| 2011/0015555 A1 | 1/2011 | Anderson et al. | |
| 2011/0021963 A1 | 1/2011 | Graddon et al. | |
| 2011/0066095 A1 | 3/2011 | Price et al. | |
| 2011/0146032 A1 | 6/2011 | Hu et al. | |
| 2011/0196275 A1 | 8/2011 | Chang et al. | |
| 2011/0313336 A1 | 12/2011 | Chan | |
| 2012/0000092 A1 | 1/2012 | Ingvarsson et al. | |
| 2012/0010534 A1 | 1/2012 | Kubiak et al. | |
| 2012/0010535 A1 | 1/2012 | Kubiak et al. | |
| 2012/0035520 A1 | 2/2012 | Ingimundarson et al. | |
| 2012/0065564 A1 | 3/2012 | Hoffmeier | |
| 2012/0078148 A1 | 3/2012 | Hu et al. | |
| 2012/0116275 A1 | 5/2012 | Pochatko | |
| 2013/0066247 A1 | 3/2013 | Bird et al. | |

(56) References Cited

U.S. PATENT DOCUMENTS

2014/0265018 A1\* 9/2014 Grim .................... A61F 5/0195
264/255

FOREIGN PATENT DOCUMENTS

| DE | 2341658 | 3/1974 |
|----|---------|--------|
| DE | 3228753 | 2/1984 |
| DE | 3909922 | 2/1990 |
| EP | 0095396 | 11/1983 |
| EP | 1006960 | 1/2003 |
| FR | 2399811 | 3/1979 |
| RU | 2165229 | 4/2001 |

OTHER PUBLICATIONS

Article from http://www.alimed.com regarding AliMed D2 Night Splint for Plantar Fasciitis.
Aircast Incorporated Product Brochure, "SP-Walker, short pneumatic walking brace", Jan. 11, 2002.
PCT Publication No. WO/2012/020251, dated Feb. 16, 2012, regarding PCT Application No. PCT/GB2011/051499.
PCT Publication No. WO/2005/097014, dated Oct. 20, 2005, regarding PCT Application No. PCT/SE2005/000513.
PCT Publication No. WO/2012/099989, dated Jul. 26, 2013, regarding PCT Application No. PCT/US2012/021763.
PCT Publication No. WO/2012/001678, dated Jan. 5, 2012, regarding PCT Application No. PCT/IL2011/000487.
Paul A. Dale, M.D. et al.; "A New Concept in Fracture Immobilization", Clinical Orthopaedics. Oct. 1993, vol. 295: 264-269.

\* cited by examiner

ORTHOPEDIC WALKING BOOT WITH HEEL CUSHION

This application claims the benefit of U.S. Provisional Patent Application Ser. Nos. 61/801,961, filed Mar. 15, 2013 and 61/916,080, filed Dec. 13, 2013, which are incorporated herein by reference.

FIELD

The present disclosure relates generally to orthopedic walking boots.

BACKGROUND

It is common that people, especially active and/or frail people, experience a variety of lower leg and ankle injuries. To aid in the treatment of the injuries it is desirable to immobilize the injury, typically above and below the affected joint.

Physicians traditionally place a patient's leg in a short leg cast, which is a cast that begins at the patient's toes and ends below the patient's knee. Generally, casts retain heat, cause an itching sensation on the skin, and rub against the leg after swelling of the leg subsides.

An alternative to the short leg cast is an orthopedic walking boot, or a premanufactured orthopedic walking boot, that is made of a rigid plastic frame lined with a soft component (e.g., a soft padding) to accommodate the leg comfortably. Often, the liner, or soft component, may house a series of air bladders that can be adjusted by the patient to improve the fit and help compress the swelling to reduce pain and increase stability. The orthopedic walking boots can be removed to treat skin problems, such as, to remove sutures or conduct passive range of motion exercises. Short leg casts do not offer the luxury of easy on/off.

An orthopedic walking boot is primarily a rigid encasing that envelopes the leg and immobilizes the foot and ankle at a neutral position (e.g., the foot extends 90 degrees relative to the leg). The patient can walk easiest if the ankle is fixed at 90 degrees. At angles other than 90 degrees the patient will be walking on the toes or on the heel. The sole of the foot is generally curved from front to back in a rocker bottom fashion. The curvature of the sole provides a smoother stride from front to back allowing the heel to strike the ground first, followed by a rocking of foot forward, and finally a push off on the toes for a successful step.

SUMMARY

Aspects of an orthopedic walking boot may include a base to support a user's foot, the base having a section configured to support the user's posterior portion of the heel; a support assembly extending from the base to support the user's lower leg; and a heel cushion arranged with said section of the base to engage the user's posterior portion of the heel, the heel portion having a free edge configured to flex.

The heel cushion may include a first portion attached to the section of the base and a second portion comprising the free edge, wherein the second portion extends from the section the base. The heel cushion may wrap around a free edge of said section of the base. The base may include opposing lateral sides extending from said section of the base, and the heel cushion may extend along an interior portion of the lateral sides. The heel cushion extending along the interior portion of the section of the base may include one or more holes or slots. The heel cushion may include a plurality of ribs or protrusions arranged to engage the user's posterior portion of the heel. The heel cushion may be overmolded to the section of the base. The orthopedic walking boot may include an outer sole, wherein the outer sole and the heel cushion comprise a continuous material overmolded to the base. The section of the base may include one or more connective tunnels through which the outer sole and heel cushion are overmolded to the base as a continuous material. The orthopedic walking boot may include one or more heel bumpers arranged with an exterior portion of said section of the base. The heel cushion and the one or more heel bumpers may comprise a continuous material overmolded to the base. The base may include an outer sole, and wherein the outer sole, the heel cushion, and the one or more heel bumpers comprise a continuous material overmolded to the base. The one or more heel bumpers may extend through one or more apertures located in the section of the base. The one or more heel bumpers may extend beyond the exterior portion.

Another aspect of an orthopedic walking boot may include a base to support a user's foot, the base having a section configured to support the user's posterior portion of the heel; a support assembly extending from the base to support the user's lower leg; and one or more heel bumpers overmolded to the base and extending beyond an exterior portion of the section.

The at least one of the one or more heel bumpers may be semi-spherical. At least one of the one or more heel bumpers is semi-ellipsoidal. At least one of the one or more heel bumpers is semi-spherical and at least another one of the one or more heel bumpers is semi-ellipsoidal.

DETAILED DESCRIPTION

Figure 1A:
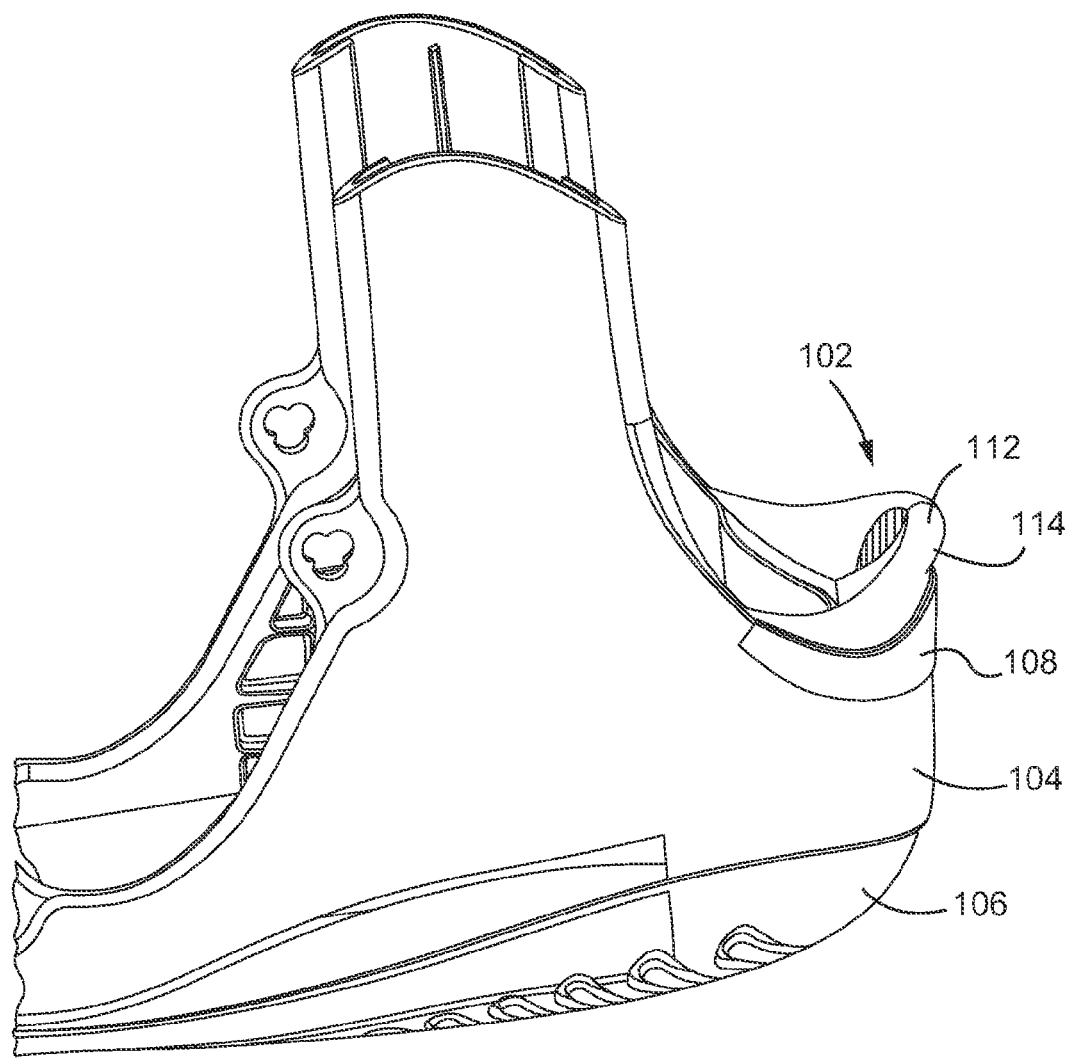
FIG. 1A is partial side perspective view of a base of an orthopedic walking boot with a heel cushion in accordance with aspects of the present invention.

Various aspects of the present invention will be described herein with reference to drawings that are schematic illustrations of idealized configurations of the present invention. As such, variations from the shapes of the illustrations as a result, for example, manufacturing techniques and/or tolerances, are to be expected. Thus, the various aspects of the present invention presented throughout this disclosure should not be construed as limited to the particular shapes of elements (e.g., regions, layers, sections, substrates, etc.) illustrated and described herein but are to include deviations in shapes that result, for example, from manufacturing. Thus, the elements illustrated in the drawings are schematic in nature and their shapes are not intended to illustrate the precise shape of an element and are not intended to limit the scope of the present invention, unless intentionally described as such.

It will be understood that when an element such as a region, layer, section, or the like, is referred to as being "on" another element, it can be directly on the other element or intervening elements may also be present. In contrast, when an element is referred to as being "directly on" another element, there are no intervening elements present. It will be further understood that when an element such as a structure is referred to as being coupled to another element, it can be directly connected to the other element or intervening elements may also be present. Similarly, two elements may be mechanically coupled by being either directly physically connected, or intervening connecting elements may be present. It will be further understood that when an element is referred to as being "formed" on another element, it can be deposited, attached, connected, coupled, or otherwise prepared or fabricated on the other element or an intervening element.

Furthermore, relative terms, such as "lower" or "bottom" and "upper" or "top," may be used herein to describe one element's relationship to another element as illustrated in the drawings. It will be understood that relative terms are intended to encompass different orientations of an apparatus in addition to the orientation depicted in the drawings. By way of example, if the orientation of an orthopedic walking boot shown in the drawings is turned over, elements described as being on the "lower" side of other elements would then be oriented on the "upper" side of the other elements. The term "lower", can therefore, encompass both an orientation of "lower" and "upper," depending of the particular orientation of the orthopedic walking boot. Similarly, if the orientation of an orthopedic walking boot shown in the drawing is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this disclosure.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The detailed description set forth below in connection with the appended drawings is intended as a description of various aspects of the present invention and is not intended to represent all aspects in which the present invention may be practiced. The detailed description includes specific details for the purpose of providing a thorough understanding of the present invention. However, it will be apparent to those skilled in the art that the present invention may be practiced without these specific details. In some instances, well-known structures and components are shown in block diagram form in order to avoid obscuring the concepts of the present invention.

Various aspects of the present invention may provide an orthopedic walking boot that may be fitted around the leg to provide support and allow ambulation for the affected limb.

Reference to various ranges may be used to describe certain aspects of the present invention. By way of example, a range may be used to describe variations of the bonding force at different points on an outer sole to describe an evenly distributed bonding of the outer sole to the base of the orthopedic walking boot. By way of an example, an outer sole which provides evenly distributed bonding to the base of the orthopedic walking boot may exhibit a narrower tolerance band of force values at all x,y coordinates on the bonding surface than tolerance band of any other attachment method of the outer sole to the base of the orthopedic walking boot.

People often experience injuries to the lower leg and ankle. For example, blunt trauma, sports injuries and common falls are the primary causes. Injuries such as fractures of the bones or soft tissue injuries (e.g., ligamentous tears) have similar symptoms. Swelling, pain and inability to ambulate without support are expected and predictable. Some injuries need to be immobilized for a period of time for the injury to heal. The time required for ligamentous injuries to heal is similar to the time required for fractures to heal. A period of 4 to 6 weeks of immobilization is common. Different injuries require different rehab times and regimes.

Aspects of the present invention are directed to orthopedic walking boots. In an aspect of the prevention invention, an orthopedic walking boot may include bilateral struts which connect a base of the orthopedic walking boot to an upper portion of the orthopedic walking boot. The struts may be rigid and provided on either side of the leg. The bilateral struts may be held onto the limb with strapping systems that encircle at least a portion of the limb. In another aspect, the base may be attached a posterior piece which extends from the foot to the back of the leg and calf forming a clamshell configuration. In the clamshell configuration, a single piece encompasses the side of the leg (similar to the bilateral configuration) as well as the rear of the leg. The orthopedic walking boot may include an adjoining anterior piece that joins or overlaps the posterior piece and is held on by a traditional strapping system or with mechanical attachment mechanism. In another aspect, the orthopedic walking boot may comprise a "hybrid" configuration (also referred herein as a "multi-sectioned" configuration). In the hybrid configuration, the base may be attached to the bilateral struts of the bilateral configuration and also attached a separate/non-integral posterior element that encompasses the rear of leg (similar to the rear portion of the clamshell). In this manner, the bilateral struts surround the side of the legs while the separate posterior portion encompasses the rear of the leg. Thus, the hybrid configuration achieves a similar result as the clamshell with multiple sections, hence, "multi-sectioned."

In an aspect, the orthopedic walking boot may be configured such that the portion that receives the user's foot (e.g., the base portion) extends at 90° degrees or at substantially 90° relative to a longitudinal axis of the portion that receives the user's leg (e.g., the upper portion). In another aspect, the orthopedic walking boot may include two struts rising from the base. The orthopedic walking boot may further include a soft component within the constraints of the struts and on top of the base. The soft component may be held by straps.

In one aspect, a relatively softer heel cushioning section of an orthopedic walking boot is described herein, which is designed to be in contact with the rear segment of a patient's anatomy in the general area of the rear of an orthopedic walking boot to reduce pain during the early stages of healing.

Users are often given instructions to elevate the injured limb whenever possible. This often means that the orthopedic walking boot needs to rest upon furniture at home such as a chair, a coffee table and similar objects where the height of the structure allows for appropriate elevation. It is often observed that most furniture has smooth hard surfaces and the resulting surface friction between a rigid plastic base of an orthopedic walking boot and said furniture is frequently low, allowing the orthopedic walking boot to slide off the furniture which may result in further injury. Furthermore, the contact between hard plastic and often delicate furniture may cause scratches, abrasion and other related damage. In an aspect of the present invention, the orthopedic walking boot provides appropriate cushion and frictional surfaces on an orthopedic walking boot, either by separate attachment through typically understood assembly techniques, or through the creation of these features through an overmolding process. The use of overmolded elastomers in a rigid plastic base allows for a multitude of features to be added at the same time the overmolded is being fabricated. Features that would not be considered in a orthopedic walking boot due to cost, quality, and/or complexity can be added for substantial enhancement in areas of ergonomics, aesthetics, functionality, low-cost part assembly, as well as additional utility.

FIG. 1A shows a partial side view of a base 104 of an orthopedic walking boot having a heel cushion 102. The orthopedic walking boot may include the base 104 and an outer sole 106. The orthopedic walking boot 100 may further include a support assembly extending from the base 104 to support the user's lower leg (not shown). The orthopedic walking boot may include an inner sole arranged with the base. The orthopedic walking boot may be a bilateral type among other types. The cushioning elements described herein may be applied to any number of different orthopedic walking boots. The heel cushion 102 may be substantially softer than the material of the base 104. For example, possible materials for the cushion may include, but are not limited to, thermoplastic elastomers (hereinafter "TPE"), thermoplastic vulcanizates (hereinafter "TPV"), silicone, rubber, gel, or any other material in the general class of flexible and formable material. The amount of flex or compliance required may be adjusted to be softer or harder by selecting a material with a particular durometer.

In one aspect, the soft elastomeric heel cushion 102 may be attached to the base 104. The heel cushion 102 may be attached to a heel portion 108 of the base 104. The soft heel cushion 102 may be permanently attached to the base by any number of means, including but not limited to adhesives, fasteners, and the like.

As shown in FIG. 1A, the heel cushion 102 may be shaped such that the free edge 112 extends outwardly (i.e., in a direction away from the toe), such that a portion of the heel cushion extends beyond the surface defined by the heel portion 108 of the base 104. In other words, if one were to if one were attempt to contact the heel portion 108 with a substantially flat surface (such as wall or table), the free edge 112 of the heel cushion 102 would contact the substantially flat surface prior to the heel portion 108 of the base contacting the surface. In an aspect, in order for the heel portion 108 of the base to contact to the substantially flat surface, force would first be applied to the heel cushion 102 to flex the free edge 112 inwardly (i.e., toward the toe).

Figure 1B:
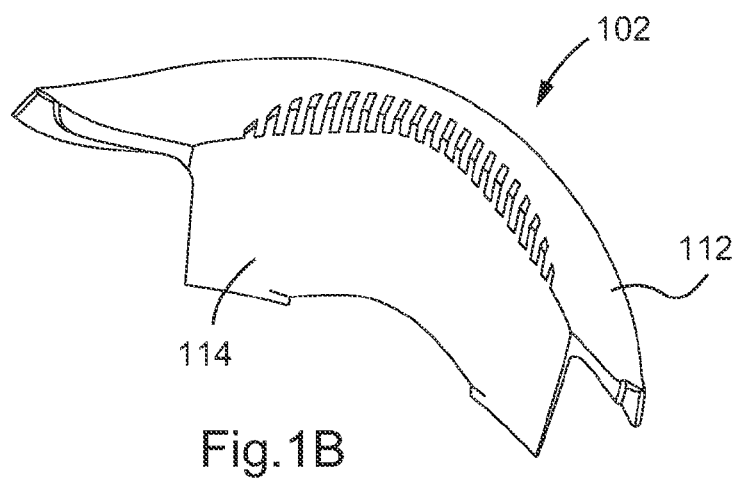
FIG. 1B is a perspective view of the heel cushion of FIG. 1A.

FIG. 1B shows a perspective view of one example aspect of the heel cushion 102 in accordance with aspects of the present invention. The heel cushion 102 may include a soft elastomeric portion/free edge 112 which may be overmolded, adhered or otherwise fastened onto a rigid plastic substrate 114. The entire assembly may be inserted into the heel portion 108 of the base 104 and assembled as discussed above, as shown in FIG. 1B. In an aspect, the rigid plastic substrate 114 may be a portion of the pre-formed base, in which case soft elastomeric portion is molded directly onto the substrate portion of pre-formed base. As shown in FIGS. 1A and 1B soft elastomeric portion 112 may define a superior free edge 112. The soft elastomeric portion 112 may be configured to flex inwardly (i.e., toward the toe) or outwardly (i.e., away from the toe) when force is applied to the soft elastomeric portion.

Figure 2:
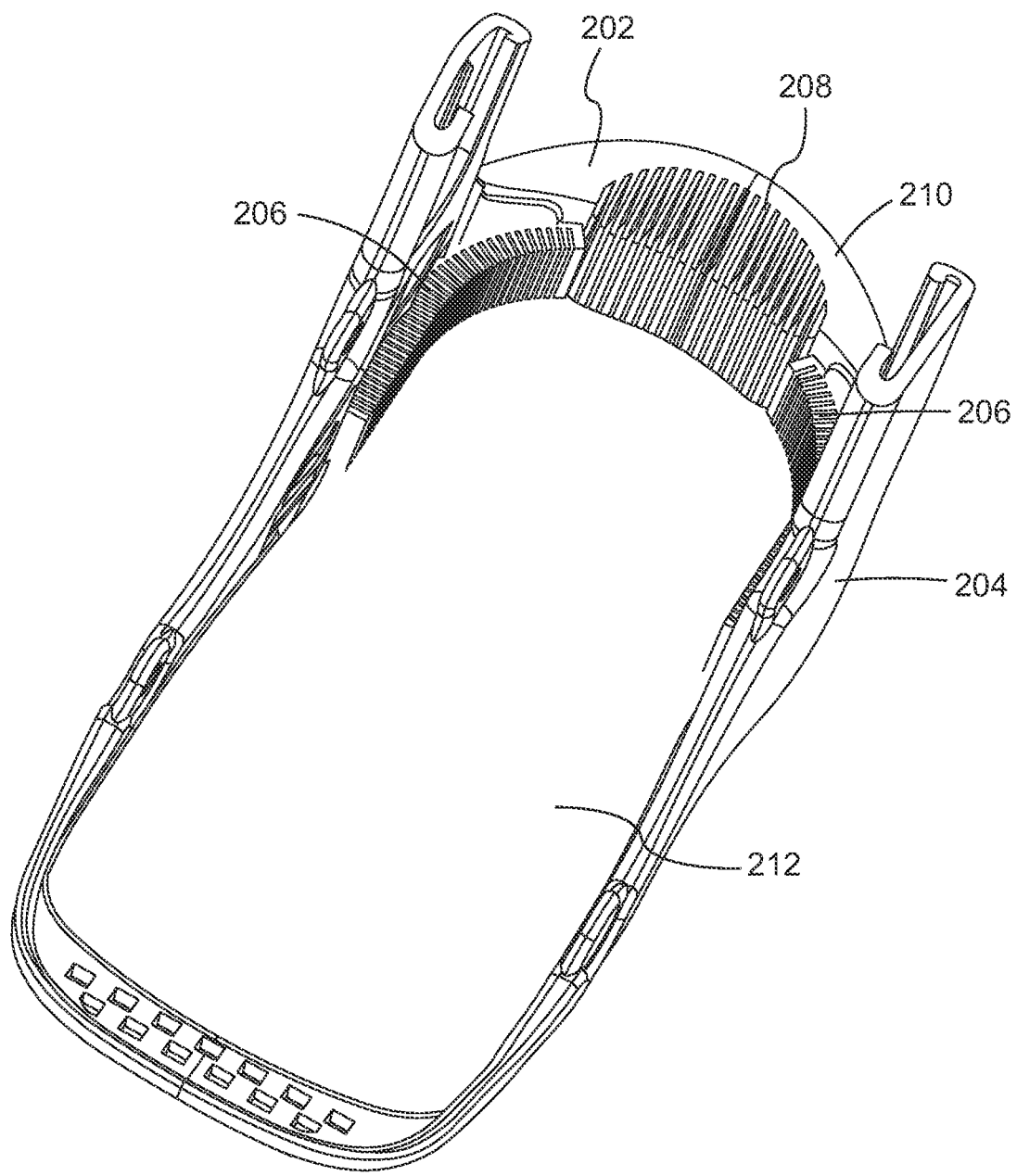
FIG. 2 is top perspective view a base of an orthopedic walking boot in accordance with other aspects of the present invention.

FIG. 2 shows a top perspective view a base 204 in accordance with another aspect of the present invention. The base 204 may include a heel cushion 202 extending to the left and right lateral sides 206 of the base 204. A rear section (also referred herein as "distal section") of the base 204 is shown in a configuration where the soft heel cushion 202 extends to the left and right lateral sides 206 of the inside of the base 204, providing additional cushion for patient physiology. In other words, the heel cushion may be arranged with a section of the base to engage the user's posterior portion of the heel and may wrap around a free edge of the section of the base. The heel cushion 102 may be attached by any number of methods familiar to those skilled in the art and may include but are not limited to overmolding, adhesives, mechanical fastening, and the like.

Additionally, the cushion 202 may include ribs 208 that extend from a free superior edge 210 of the cushion to an insole plate 212. The free edge 210 may be configured to flex inwardly (i.e., toward the toe) or outwardly (i.e., away from the toe) when force is applied to the cushion 202.

Figure 3A:
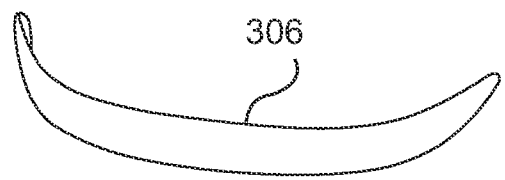
FIGS. 3A-3D are rear perspective views of various heel cushions in accordance with aspects of the present invention.
Figure 3B:
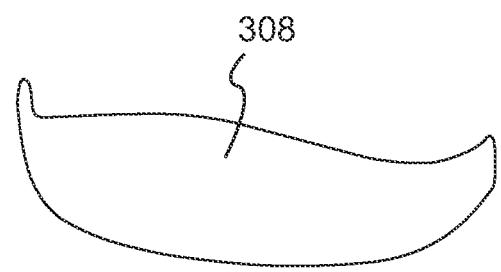
Figure 3C:
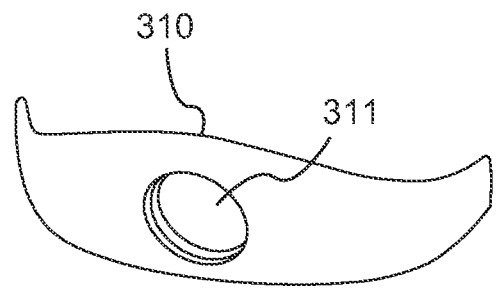
Figure 3D:
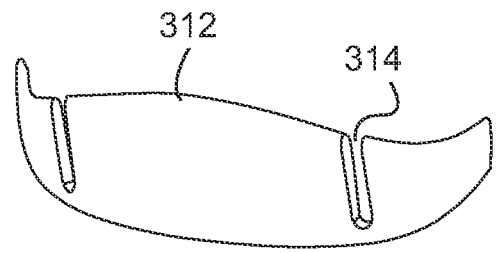

The aspects described herein do not serve to limit the specific geometry of a heel cushion. Rather a wide variety of possible geometries are possible, including but not limited to those shown in FIGS. 3A-3D. FIGS. 3A-3D are rear views of various geometries for a heel cushion in accordance with aspects of the present invention. The geometries shown in FIGS. 3A-3D are examples, and do not limit the possible configurations derived by someone skilled in the art. FIG. 3A shows a low-profile shaped heel cushion 306. FIG. 3B shows a high profile shaped heel cushion 309. FIG. 3C shows a heel cushion 310 having at least a single hole 311 extending through the heel cushion. The heel cushion 310 may also include a plurality of holes. The single hole or the plurality of holes may either partially or completely extend through the heel cushion. The hole 311 may provide a higher deflection in specific areas. The number of holes, hole geometry, or depth of cut, is not limited to and the heel cushion may include a variety of holes with a variety of depths depending on the utility of a particular orthopedic walking boot. For example, the additional utility may include providing higher deflection in specific areas. FIG. 3D shows a heel cushion 312 including a plurality of segments or slots 314. The plurality of segments 314 may allow for varying mechanical properties and comfort to the wearer in specific zones.

Figure 4A:
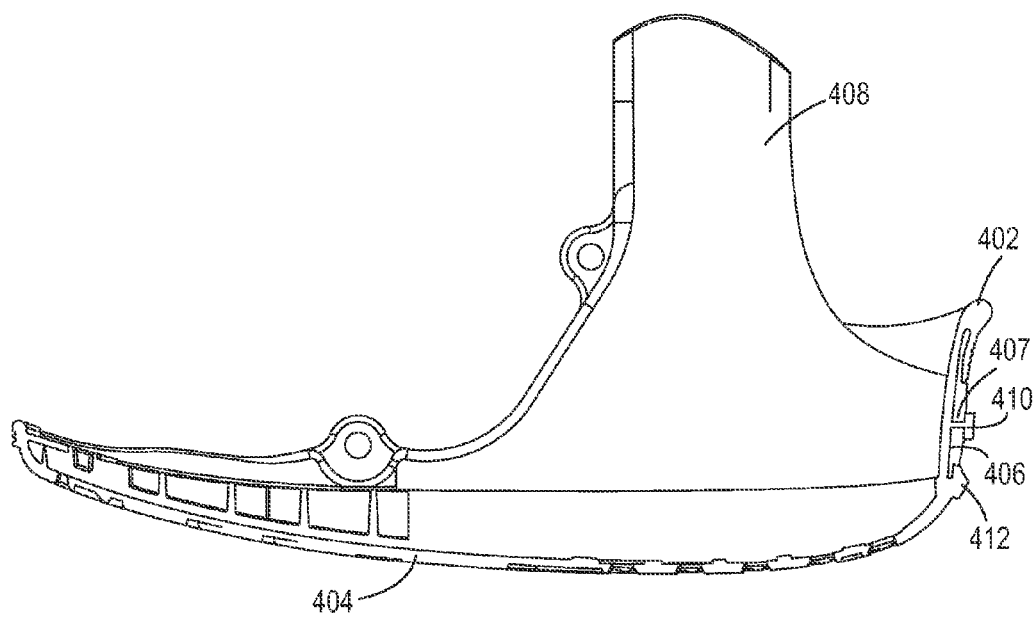
FIG. 4A is a side view of a base with a heel bumper in accordance with aspects of the present invention.
Figure 4B:
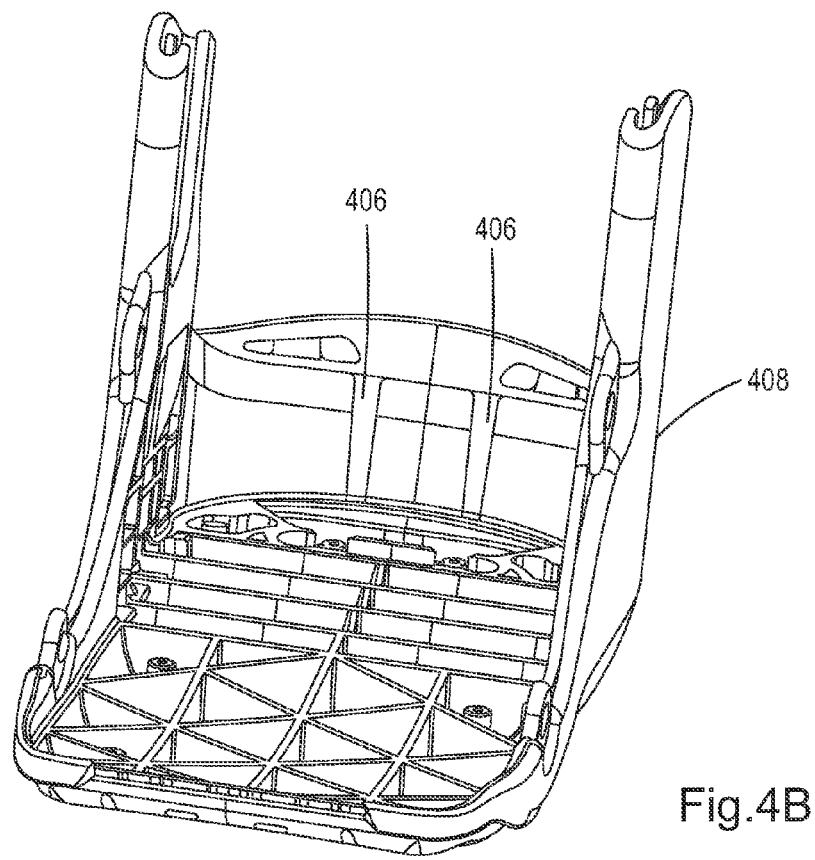
FIG. 4B is a front perspective view of the base of FIG. 4A prior to molding a heel cushion onto the base.

FIG. 4A is a side cross section view showing a base 408 of an orthopedic walking boot, having an outer sole 404 overmolded onto the base 408. As shown in FIG. 4A, the heel portion may include a bumper 410 protruding from the heel portion. The heel portion may also include a secondary heel bumper 412 located below the bumper 410 (i.e., closer to the ground when the base is upright). The outer sole 404 may be fabricated from any number of different materials including but not limited to rubber, silicone, TPV, TPE, gel, and the like. In one aspect, the soft heel 402 may be created at the same time as the outer sole 404 via a connective tunnel 406 disposed within the wall thickness of the base 408. An aperture 407 may extend through the thickness of the heel portion and communicate with the connective tunnel 406. The bi-directionality of the flow of molten material may allow gating of the elastomer at the heel section 402 while the outer sole 404 is filled subsequently through the connective tunnel 406 and aperture 407. FIG. 4A shows the connective channel 406 and the aperture 407 filled with resin. FIG. 4B shows the base of FIG. 4A prior to overmolding the outer sole onto the base and prior to forming the heel cushion. As seen in FIG. 4B, prior to the process of overmolding of the outer sole 404 to the base 408, the connective channel 406 (and the aperture, not shown) would not be filled with resin. When the resin of the outer sole passes through the connecting tunnel and the aperture to form the heel cushion and the heel bumper, the outer sole, the heel cushion, and the heel bumper all comprise the same continuous material. In an aspect, the outer sole, the heel cushion, and the heel bumper can be formed through as single injection molding shot process.

Figure 4C:
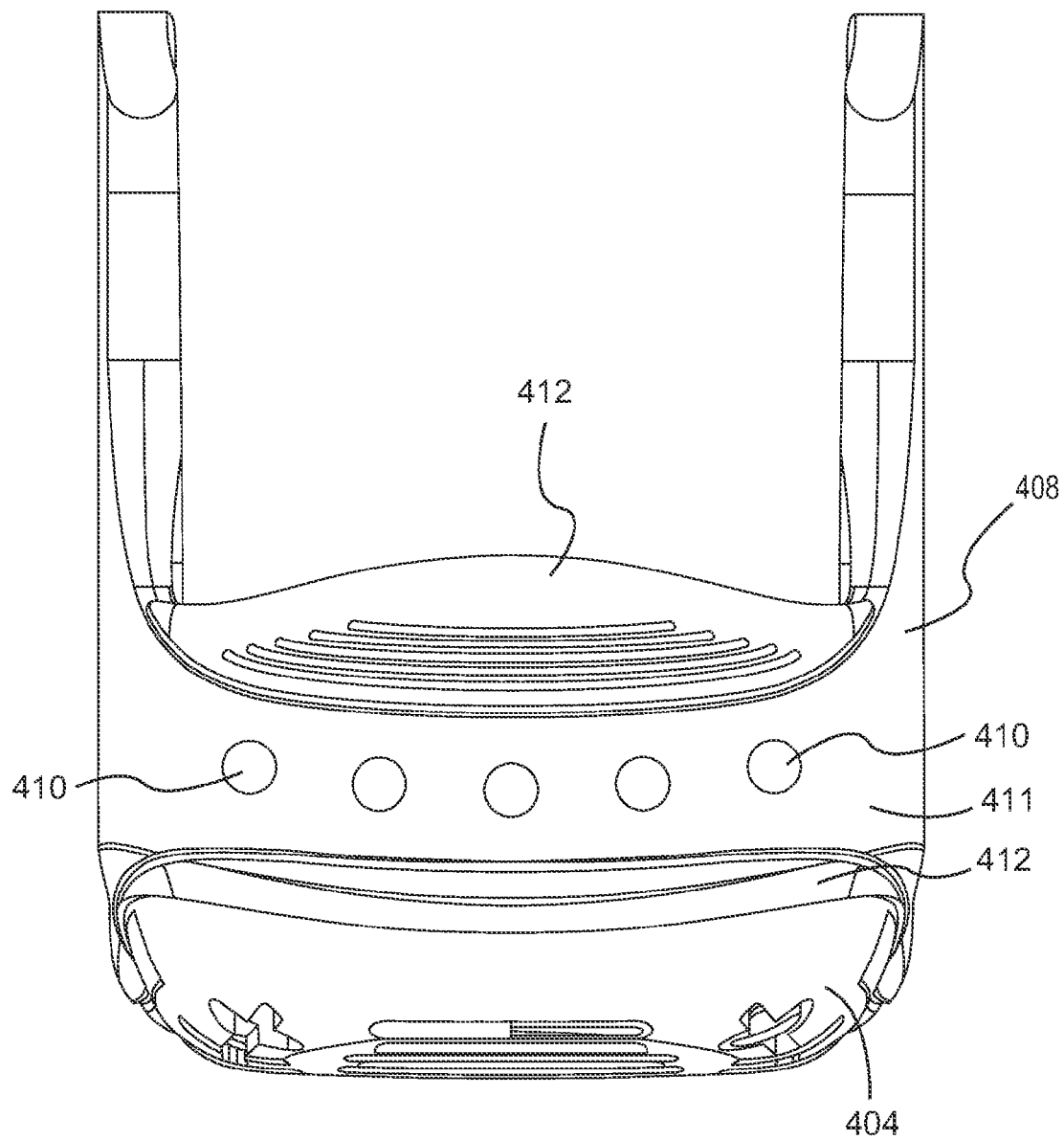
FIGS. 4C and 4D are rear views of various heels with bumpers in accordance with other aspects of the present invention.
Figure 4D:
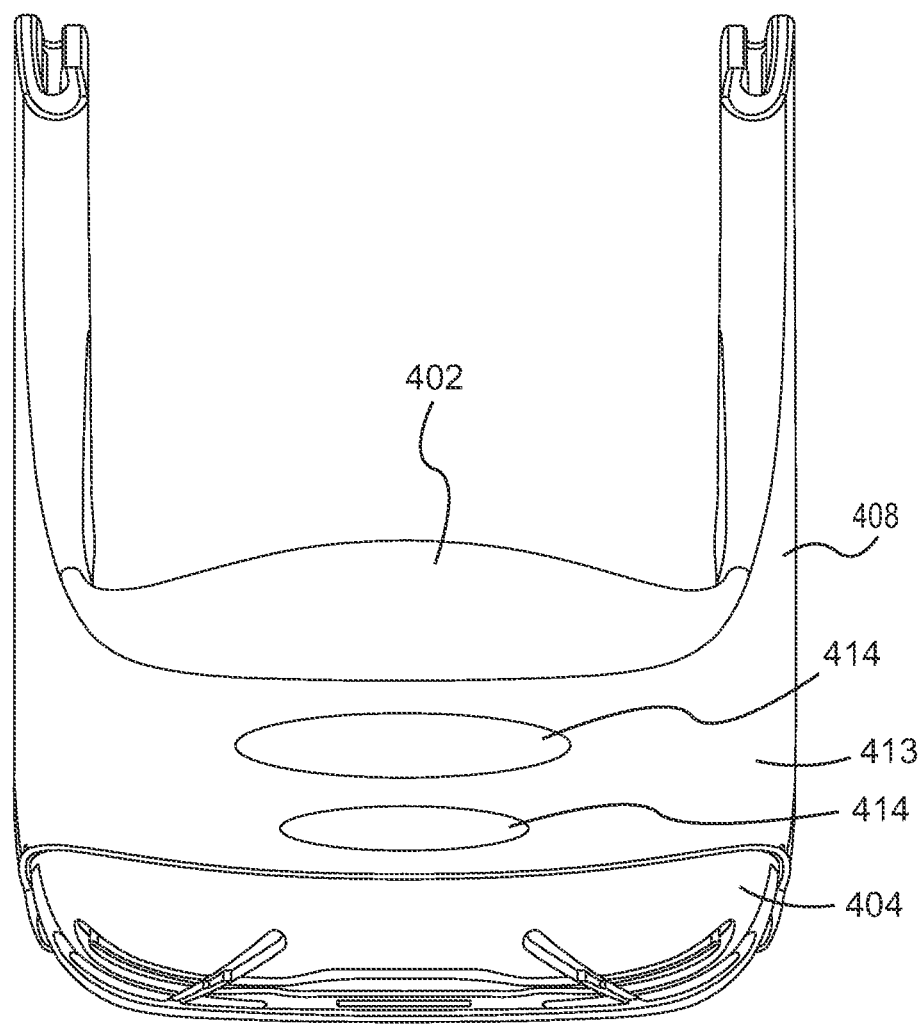

FIG. 4C shows a rear view of the base with outer sole and heel cushion formed thereon. In an aspect, the heel portion may include a plurality of bumpers in any number of shapes and sizes and spacing densities. For example, as shown in FIG. 4C, the heel portion 411 may include a plurality of bumpers 412 arranged in a substantially horizontal row. FIG. 4C also shows the secondary bumper 412 discussed above. FIG. 4D shows a second example aspect of the base 408 having the heel cushion 402 and outer sole 404, where a heel portion 413 includes vertically oriented bumpers 414. In addition, the bumpers 410, 412, 414 may be produced as a separate attachment, and adhered to the heel portion.

Figure 5A:
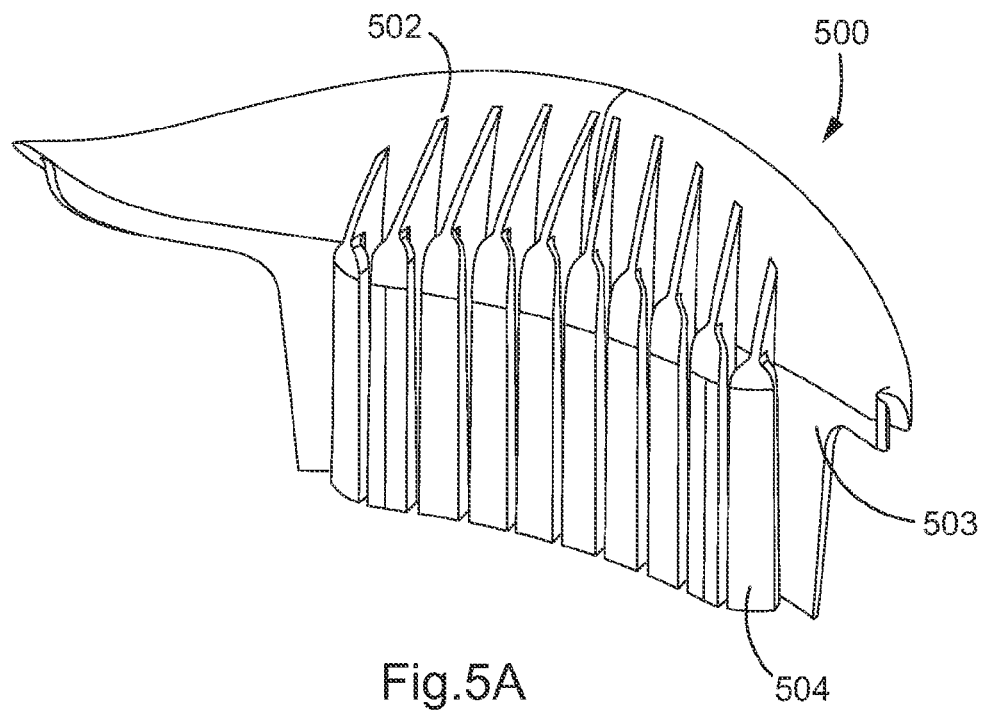
FIGS. 5A, 5C, 5E, and 5G are various perspective views of heel cushions in accordance with aspects of the present invention.
Figure 5B:
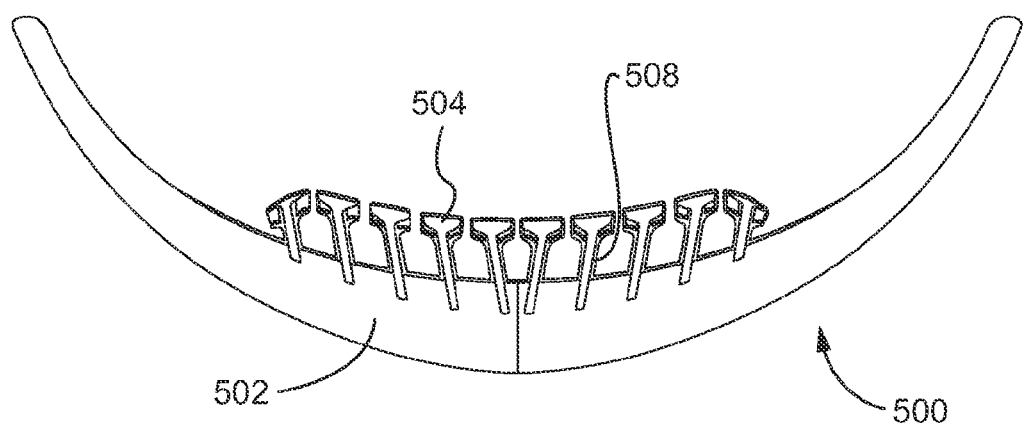
FIG. 5B is a top view of the heel cushion of FIG. 5A.

FIGS. 5A to 5E show a variety of example of heel cushions in accordance with aspects of the present invention. FIG. 5A shows a perspective view and FIG. 5B shows a top view of a heel cushion 500. As shown in FIGS. 5A and 5B, the heel cushion 500 may include an elastomeric portion 502 at an upper perimeter (i.e., the free edge), a substrate 503, and flexible ribs 504. The ribs 504 may comprise a flexible material such as rubber, aligned vertically towards the inside portion of the heel cushion 500 and extending from the substrate 503. The inner surface of the heel cushion may feature a pattern of ribs that allows localized deflection to accommodate a patient specific physiological need. As shown in FIG. 5B, the vertical ribs 504 join to the elastomeric portion 502 with a smaller cross-section area 508, allowing the ribs 504 to move laterally as well as deflect away from the user's heel towards the back of the orthopedic walking boot. The ribs 504 may include broader portions 506. Additionally, the broader portions 506 may allow for lower pressure applied to the patient's physiology, resulting in higher overall comfort.

Figure 5C:
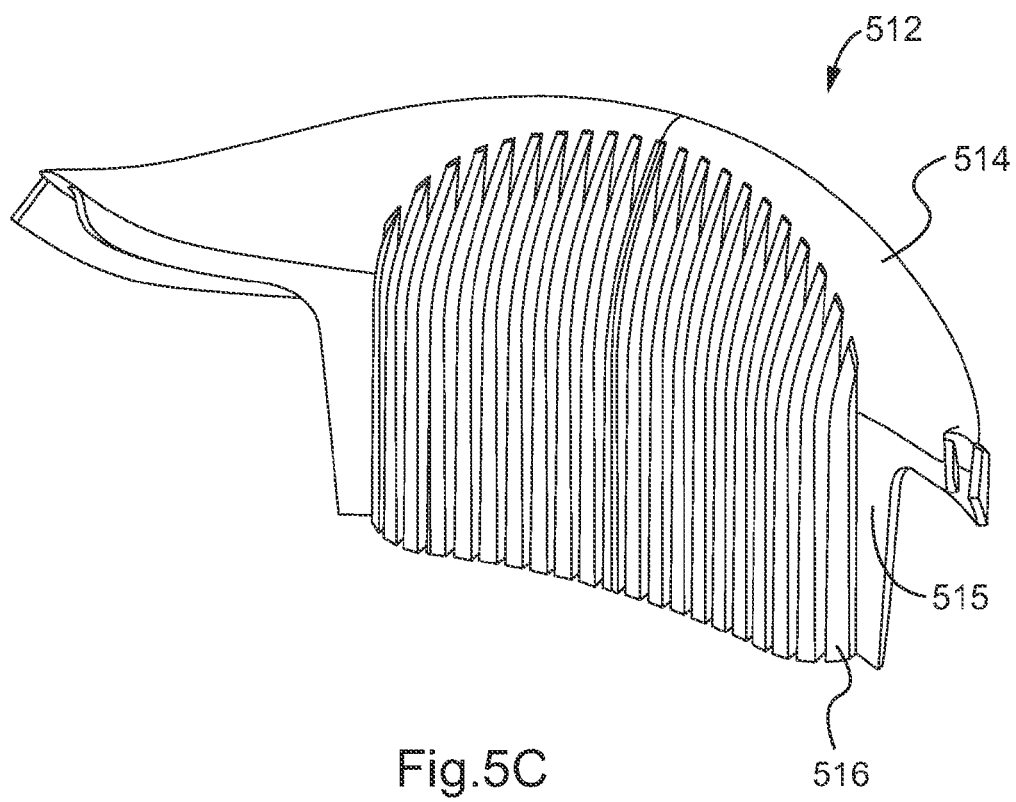
Figure 5D:
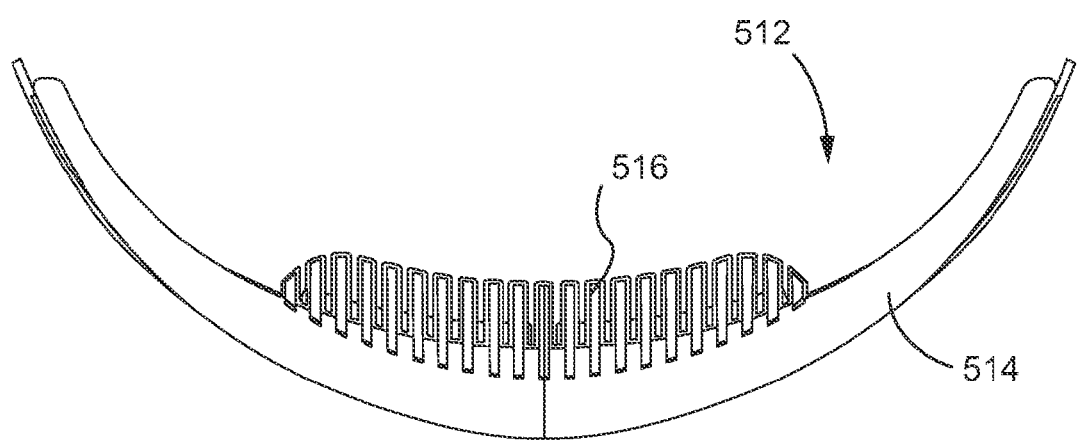
FIG. 5D is a top view of the heel cushion of FIG. 5C.

FIG. 5C shows a perspective view and FIG. 5D shows a top view of a heel cushion 512. As shown in FIGS. 5C and 5D, the heel cushion 512 includes an elastomeric portion 514, a substrate 515, and a plurality of parallel ribs 516. The plurality of ribs 516 may extend from the substrate 515 and include cross section sufficiently thin to allow for motion relative to the soft heel cushion 514 upon relatively low force imparted by contacting patient physiology. The geometry of ribs 514 shown in FIGS. 5A and 5B should not be construed to limit in any way the possible configurations which achieve the same end result of compliance to the presence of a patient's heel. The vertical profile of the plurality of ribs 516 may follow a mainly constant curvature such as shown in FIG. 5D or may have a curvature that more closely conforms to the physiology of the human heel allowing for more clearance in the geometric center of the pattern where the Achilles tendon is naturally located.

Figure 5E:
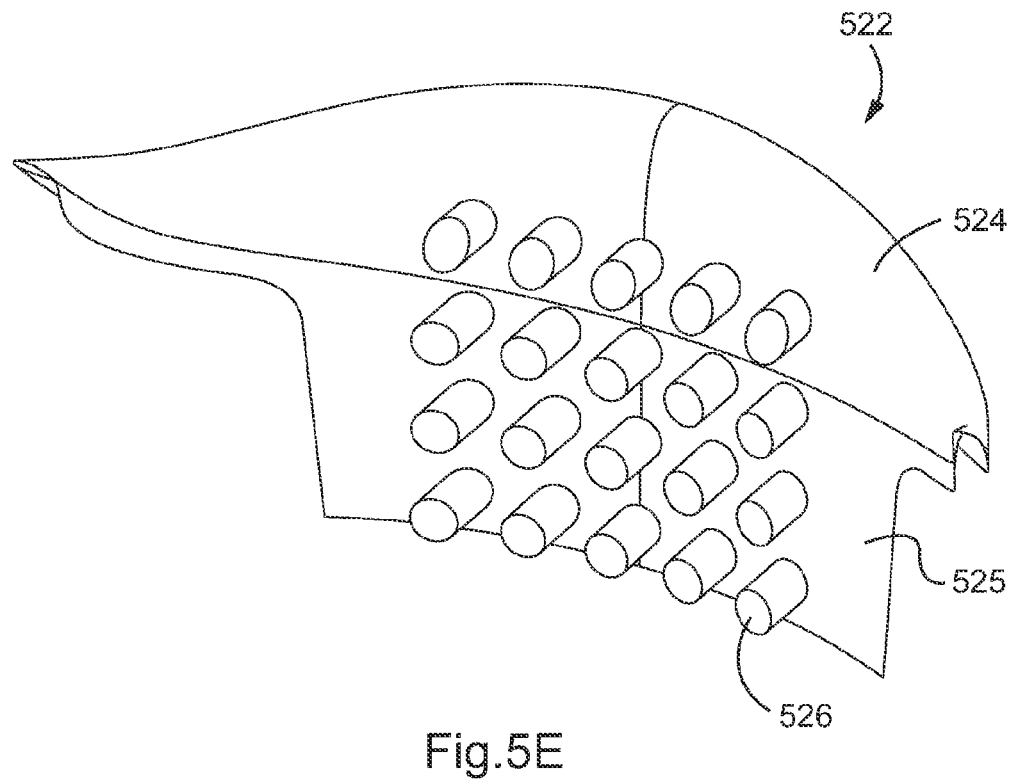
Figure 5F:
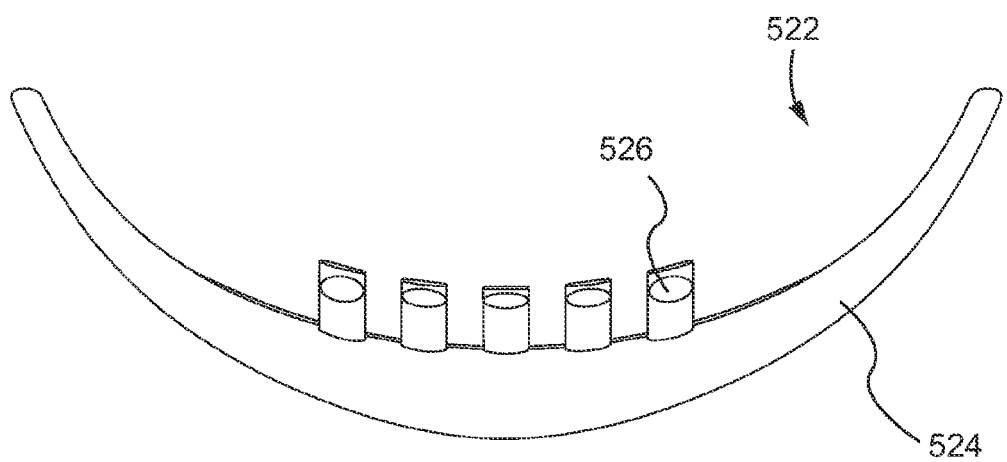
FIG. 5F is a top view of the heel cushion of FIG. 5E.

FIG. 5E shows a perspective view of a heel cushion 512. The heel cushion 522 may include an elastomeric portion 524 at an upper perimeter (i.e., the free edge) of the cushion, a substrate 525, and a plurality of protrusions 526 extending substantially normal to the substrate 525. While FIG. 5E shows protrusions that are cylindrical in shape, other geometries, feature densities, and locations may be utilized.

Figure 5G:
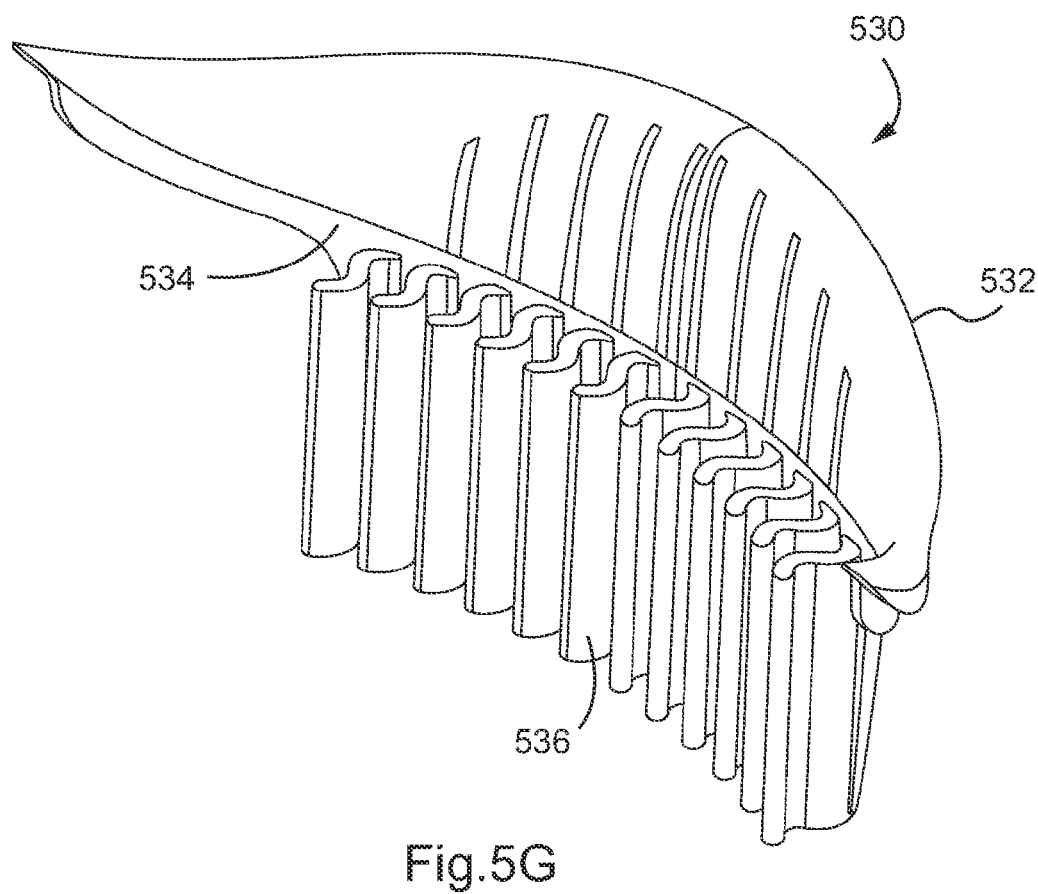
Figure 5H:
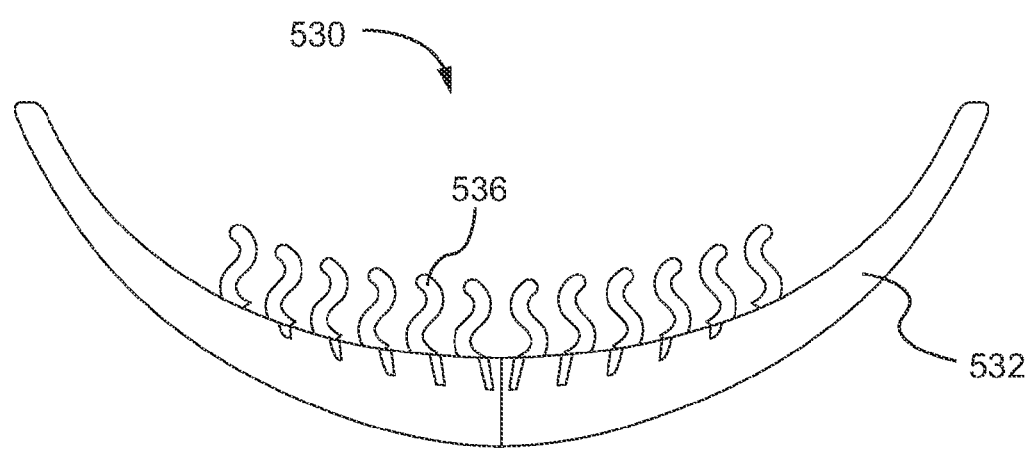
FIG. 5H is a top view of the heel cushion of FIG. 5G.

FIG. 5G shows a perspective view and FIG. 5H shows a top view of a heel cushion 530. As shown in FIGS. 5G and 5H, the cushion 350 may include an elastomeric portion 532 at an upper perimeter (i.e., the free edge), a substrate 534, and ribs 536 that provide a spring function. The ribs 536 may include a plurality of vertical ribs that may be fabricated as part of the heel cushion 530 where each rib features specific cross section geometry that may allow the rib to act in a similar manner as a spring when force is applied to the rib. The particular cross sectional geometry used to perform the desired action may be of any number of variations, and may feature multiple transitions within each cross-sectional profile of the ribs used. It should also be noted that cross-sectional profile may vary from rib to adjacent rib laterally as well as vertically.

Although the embodiments described have been disclosed in the context of exemplary embodiments and examples, it will be understood by those skilled in the art that the embodiments described herein extend beyond the specifically disclosed embodiments to other alternate embodiments and/or uses and obvious modifications and equivalents thereof. Thus, it is intended that the scope of the embodiments described herein disclosed should not be limited by the particular disclosed embodiments described above.

The claims are not intended to be limited to the various aspects of this disclosure, but are to be accorded the full scope consistent with the language of the claims. It is noted that specific illustrative embodiments of the invention have been shown in the drawings and described in detail hereinabove. It is to be understood that various changes and modifications may be made without departing from the spirit and scope of the invention. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An orthopedic walking boot, comprising:
   a base to support a user's foot, the base having a section configured to support a posterior portion of the user's heel;
   a support assembly extending from the base to support the user's lower leg; and
   a heel cushion arranged with said section of the base to engage the user's posterior portion of the heel, the heel portion having a free edge configured to flex, wherein the heel cushion is overmolded to said section of the base.

2. The orthopedic walking boot of claim 1, wherein the heel cushion comprises a first portion attached to the section of the base and a second portion comprising the free edge, wherein the second portion extends from the section the base.

3. The orthopedic walking boot of claim 1 wherein the heel cushion wraps around a free edge of said section of the base.

4. The orthopedic walking boot of claim 1 wherein the base further comprises opposing lateral sides extending from said section of the base, and wherein the heel cushion extends along an interior portion of the lateral sides.

5. The orthopedic walking boot of claim 4 wherein the heel cushion extending along the interior portion of said section of the base comprises one or more holes or slots.

6. The orthopedic walking boot of claim 1 wherein the heel cushion comprises a plurality of ribs or protrusions arranged to engage the user's posterior portion of the heel.

7. The orthopedic walking boot of claim 1 further comprising an outer sole, wherein the outer sole and the heel cushion comprise a continuous material overmolded to the base.

8. The orthopedic walking boot of claim 7 wherein said section of the base comprises one or more connective tunnels through which the outer sole and heel cushion are overmolded to the base as a continuous material.

9. An orthopedic walking boot, comprising:
   a base to support a user's foot, the base having a section configured to support a posterior portion of the user's heel;
   a support assembly extending from the base to support the user's lower leg; and
   a heel cushion arranged with said section of the base to engage the user's posterior portion of the heel, the heel portion having a free edge configured to flex,
   one or more heel bumpers arranged with an exterior portion of said section of the base, wherein the heel cushion and the one or more heel bumpers comprise a continuous material overmolded to the base.

10. The orthopedic walking boot of claim 9 wherein the base further comprises an outer sole, and wherein the outer sole, the heel cushion, and the one or more heel bumpers comprise a continuous material overmolded to the base.

11. The orthopedic walking boot of claim 9 wherein the one or more heel bumpers extend through one or more apertures located in the section of the base.

12. The orthopedic walking boot of claim 9 wherein the one or more heel bumpers extend beyond the exterior portion.

13. An orthopedic walking boot, comprising:
    a base to support a user's foot, the base having a section configured to support a posterior portion of the user's heel;
    a support assembly extending from the base to support the user's lower leg; and
    one or more heel bumpers overmolded to the base and extending beyond an exterior portion of the section.

14. The orthopedic walking boot of claim 13 wherein at least one of the one or more heel bumpers is semi-spherical.

15. The orthopedic walking boot of claim 13 wherein at least one of the one or more heel bumpers is semi-ellipsoidal.

16. The orthopedic walking boot of claim 13 wherein at least one of the one or more heel bumpers is semi-spherical and at least another one of the one or more heel bumpers is semi-ellipsoidal.

17. The orthopedic walking boot of claim 13 further comprising an outer sole, wherein the one or more bumpers and the outer sole comprise a continuous material overmolded to the base.

18. The orthopedic walking boot of claim 13 wherein the one or more heel bumpers extend through one or more apertures located in the section of the base.

* * * * *